(12) United States Patent
Tsai

(10) Patent No.: US 9,415,199 B2
(45) Date of Patent: Aug. 16, 2016

(54) LEAK PROOF NEEDLELESS MEDICAL CONNECTOR

(71) Applicant: Hsi-Chin Tsai, New Taipei (TW)

(72) Inventor: Hsi-Chin Tsai, New Taipei (TW)

(73) Assignee: SKILL PARTNER LIMITED, Apia (WS)

( * ) Notice: Subject to any disclaimer, the term of this patent is extended or adjusted under 35 U.S.C. 154(b) by 265 days.

(21) Appl. No.: 13/918,404

(22) Filed: Jun. 14, 2013

(65) Prior Publication Data

US 2014/0371724 A1    Dec. 18, 2014

(51) Int. Cl.
| | |
|---|---|
| *A61M 39/00* | (2006.01) |
| *A61M 39/10* | (2006.01) |
| *A61M 39/26* | (2006.01) |
| *A61M 39/24* | (2006.01) |

(52) U.S. Cl.
CPC ............... *A61M 39/10* (2013.01); *A61M 39/26* (2013.01); *A61M 2039/1033* (2013.01); *A61M 2039/1077* (2013.01); *A61M 2039/2433* (2013.01); *A61M 2039/2473* (2013.01); *A61M 2039/268* (2013.01)

(58) Field of Classification Search
CPC .......... A61M 39/26; A61M 2039/263; A61M 2039/267; A61M 39/02; A61M 39/10; A61M 39/22; A61M 5/504; A61M 5/30; Y10S 128/912; Y10S 128/06
See application file for complete search history.

(56) References Cited

U.S. PATENT DOCUMENTS

| | | | | |
|---|---|---|---|---|
| 5,788,215 A | * | 8/1998 | Ryan ........................... | 251/149.6 |
| 6,039,302 A | * | 3/2000 | Cote et al. .................. | 251/149.1 |
| 6,183,448 B1 | * | 2/2001 | Mayer .......................... | 604/256 |
| 6,964,406 B2 | * | 11/2005 | Doyle ......................... | 251/149.6 |
| 7,125,396 B2 | * | 10/2006 | Leinsing et al. ......... | 604/167.03 |
| 7,497,848 B2 | * | 3/2009 | Leinsing et al. ............... | 604/247 |
| 8,105,314 B2 | * | 1/2012 | Fangrow, Jr. .................. | 604/533 |
| 8,211,069 B2 | * | 7/2012 | Fangrow, Jr. .................. | 604/256 |
| 8,568,371 B2 | * | 10/2013 | Siopes et al. .................. | 604/256 |
| 8,628,516 B2 | * | 1/2014 | Naftalovitz et al. .......... | 604/537 |
| 8,679,090 B2 | * | 3/2014 | Anderson et al. ............. | 604/533 |
| 8,758,306 B2 | * | 6/2014 | Lopez et al. .................. | 604/247 |

(Continued)

FOREIGN PATENT DOCUMENTS

| | | |
|---|---|---|
| JP | 2001212235 A | 8/2001 |
| JP | 3185806 U | 9/2013 |

(Continued)

OTHER PUBLICATIONS

Japan Patent Office, Office Action issued on Sep. 15, 2015.
European Patent Office, European Search Report issued on Jan. 8, 2014.

*Primary Examiner* — Scott Medway
(74) *Attorney, Agent, or Firm* — Rabin & Berdo, P.C.

(57) ABSTRACT

A leak proof needleless medical connector has a housing, an actuator, a resilient member and an adapter. The housing includes a valve tube. The valve tube has a bottom annular blocking projection extending from an inner surface thereof. The actuator and the resilient member are mounted in the housing and the adapter is mounted on a top of the housing. A bottom valve stem is mounted in the valve tube of the housing. A gap is formed between the bottom valve stem and the valve tube. A bottom end of the bottom valve stem abuts the bottom annular blocking projection of the valve tube to close an open bottom of the valve tube. In use, a dosing unit is screwed into the needleless medical connector. Thus, a flow channel is formed within the needleless medical connector and the dosing unit to allow passage of medication.

20 Claims, 25 Drawing Sheets

(56) References Cited

U.S. PATENT DOCUMENTS

| | | | |
|---|---|---|---|
| 2003/0050610 A1* | 3/2003 | Newton et al. | 604/256 |
| 2004/0124388 A1* | 7/2004 | Kiehne | 251/149.1 |
| 2005/0087715 A1* | 4/2005 | Doyle | 251/149.1 |
| 2006/0142735 A1* | 6/2006 | Whitley | 604/537 |
| 2006/0161115 A1* | 7/2006 | Fangrow | 604/249 |
| 2006/0264841 A1* | 11/2006 | Cote et al. | 604/247 |
| 2008/0172003 A1* | 7/2008 | Plishka et al. | 604/249 |
| 2012/0059334 A1 | 3/2012 | Pan | |
| 2012/0277688 A1 | 11/2012 | Rogier | |

FOREIGN PATENT DOCUMENTS

| | | |
|---|---|---|
| WO | WO-2006062912 A1 | 6/2006 |
| WO | WO-2006078355 A1 | 7/2006 |
| WO | WO-2010071848 A1 | 6/2010 |
| WO | WO-2010127461 A1 | 11/2010 |
| WO | WO-2011064738 A2 | 6/2011 |

* cited by examiner

LEAK PROOF NEEDLELESS MEDICAL CONNECTOR

BACKGROUND OF THE INVENTION

1. Field of the Invention

The present invention relates generally to medical injectors, and more particularly to a needleless medical connector for preventing leakage of medication.

2. Description of the Related Art

A medical injector is used to inject medication into a patient. A conventional medical injector comprises a syringe fitted with a needle. Medication is injected from the syringe into a patient through the needle. However, the needle is unsafe and medical personnel may accidentally get stabbed by the needle. Accordingly, a needleless medical injector without using a needle has been developed.

When the needleless medical injector is in use, a needleless medical connector is screwed into the needleless medical injector and a dosing unit is then screwed into the needleless medical connector. Thus, a flow channel is formed within the needleless medical connector and the dosing unit to allow passage of medication and injection of the medication into a patient. After the necessary medication has been dispensed, the dosing unit is removed from the needleless medical connector. However, current needleless medical connectors have poor sealing property such that leakage of the medication may occur when the dosing unit is removed.

To overcome the shortcomings, the present invention provides a leak proof needleless medical connector to mitigate or obviate the aforementioned problems.

SUMMARY OF THE INVENTION

The present invention provides a leak proof needleless medical connector that can prevent leakage of medication.

A leak proof needleless medical connector in accordance with the present invention comprises a housing, an actuator, a resilient member and an adapter. The housing includes a valve tube. The valve tube has a bottom annular blocking projection extending from an inner surface of the valve tube. The actuator is movably disposed within the housing. The resilient member is disposed within the housing and includes in sequence a lower compression tube, a column and an upper compression tube. The lower compression tube and the upper compression tube are resiliently compressible and expansible. The column has at least one through hole defined therethrough. An interior of the lower compression tube communicates with an interior of the upper compression tube through the at least one through hole of the column. A bottom valve stem is disposed in the lower compression tube. The lower compression tube is mounted around the valve tube of the housing and the bottom valve stem is mounted in the valve tube. A gap is formed between the bottom valve stem and the valve tube. The gap does not communicate with the interior of the upper compression tube. A bottom end of the bottom valve stem abuts the bottom annular blocking projection of the valve tube to close an open bottom of the valve tube. A top valve stem is disposed in the upper compression tube. The adapter is mounted on a top of the housing such that the resilient member is mounted between the adapter and the actuator. An interior of the adapter does not communicate with the at least one through hole of the column because of the said top valve stem. In use, a dosing unit is screwed into the needleless medical connector. Thus, a flow channel is formed within the needleless medical connector and the dosing unit to allow passage of medication.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
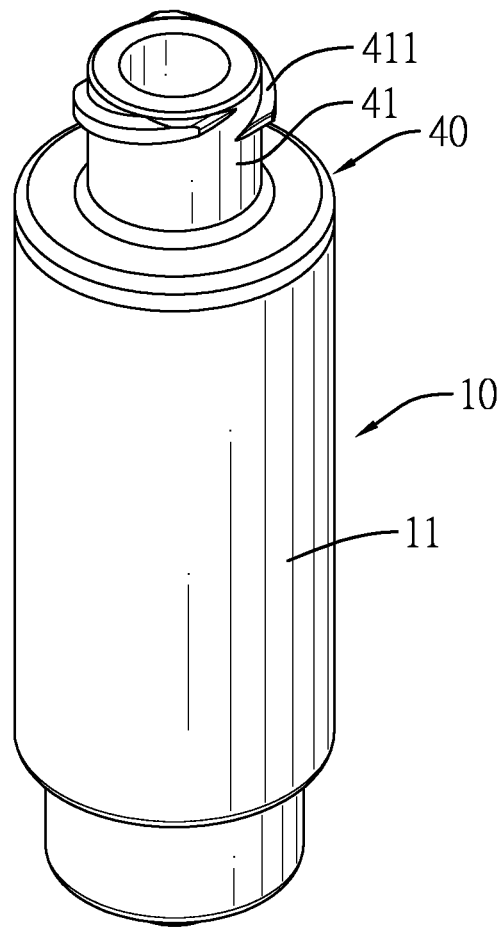
FIG. 1 is a perspective view of a first embodiment of the leak proof needleless medical connector in accordance with the present invention.
Figure 2:
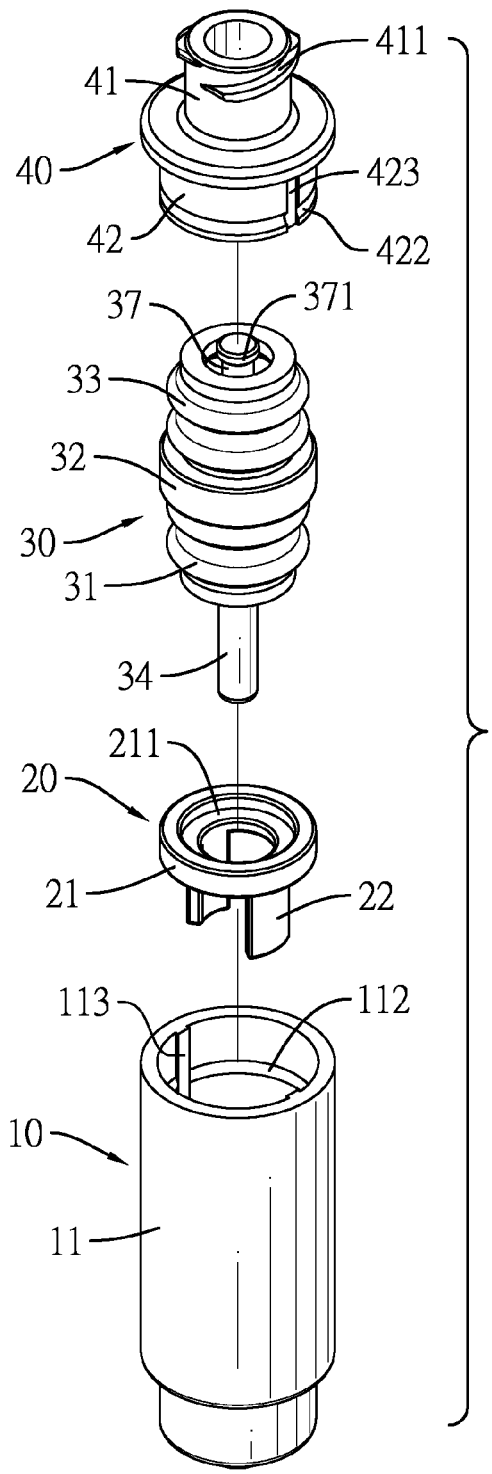
FIG. 2 is an exploded perspective view of the leak proof needleless medical connector in FIG. 1.
Figure 3:
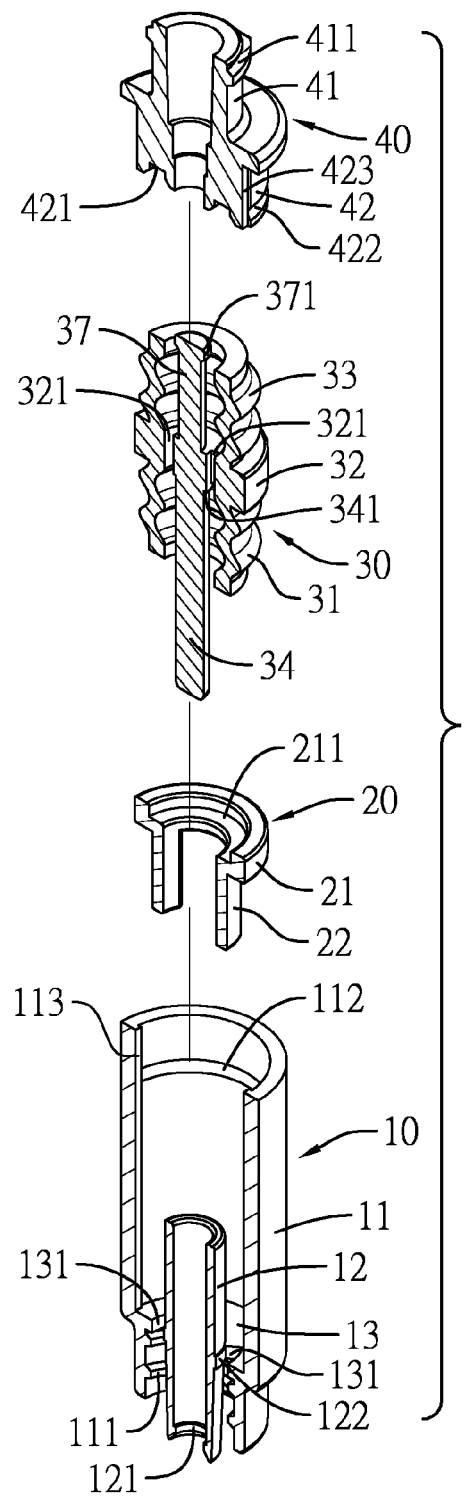
FIG. 3 is an exploded cross-sectional perspective view of the leak proof needleless medical connector in FIG. 1.

With reference to FIGS. 1 to 4, a leak proof needleless medical connector in accordance with the present invention comprises a housing 10, an actuator 20, a resilient member 30 and an adapter 40.

The housing 10 includes an outer casing 11, a valve tube 12 and an annular portion 13. A bottom portion of the outer casing 11 is provided with internal threads 111. The valve tube 12 is disposed within the outer casing 11 and adjacent to the internal threads 111, and the valve tube 12 has an inner surface, an outer surface, a bottom annular blocking projection 121 and an abutting ring 122. The bottom annular blocking projection 121 extends from a bottom end of the inner surface of the valve tube 12. The abutting ring 122 extends from the outer surface of the valve tube 12. The annular portion 13 is formed between the outer casing 11 and the valve tube 12 and has a plurality of longitudinal guide holes 131 defined therethrough.

The actuator 20 is hollow, is movably disposed within the outer casing 11 of the housing 10 and includes a collar 21 and a plurality of guide members 22. The collar 21 is mounted around the valve tube 12 of the housing 10 above the annular portion 13 and has a top surface, a bottom surface and a first annular receiving groove 211. The first annular receiving groove 211 is formed in the top surface of the collar 21. The guide members 22 extend downward from the bottom surface of the collar 21. The guide members 22 correspond to and are inserted respectively through the guide holes 131 of the annular portion 13 of the housing 10 to allow the actuator 20 to move longitudinally only within the housing 10. The abutting ring 122 of the valve tube 12 of the housing 10 abuts inner surfaces of the guide members 22.

The resilient member 30 is disposed within the outer casing 11 of the housing 10 above the actuator 20 and includes in sequence a lower compression tube 31, a column 32 and an upper compression tube 33. The lower compression tube 31 and the upper compression tube 33 are resiliently compressible and expansible. The column 32 has at least one longitudinal through hole 321 defined therethrough. An interior of the lower compression tube 31 communicates with an interior of the upper compression tube 33 through the at least one through hole 321 of the column 32. The lower compression tube 31 is mounted around the valve tube 12 of the housing 10 and a bottom end of the lower compression tube 31 is received in the first annular receiving groove 211 of the collar 21 of the actuator 20. A space 35 is formed between the valve tube 12 and the lower compression tube 31. A top end of an inner surface of the lower compression tube 31 abuts a top end of the outer surface of the valve tube 12 such that the space 35 does not communicate with the at least one through hole 321 of the column 32. A bottom valve stem 34 is disposed in the lower compression tube 31 and is mounted in the valve tube 12. A gap 36 is formed between the bottom valve stem 34 and the valve tube 12. The gap 36 does not communicate with the interior of the upper compression tube 33. A bottom end of the bottom valve stem 34 abuts the bottom annular blocking projection 121 of the valve tube 12 to close an open bottom of the valve tube 12. A top valve stem 37 is disposed in the upper compression tube 33.

The adapter 40 is hollow, is mounted on a top of the outer casing 11 of the housing 10 and includes a top annular member 41 and a bottom annular member 42. The top annular member 41 is provided with external threads 411. The bottom annular member 42 is inserted into the top of the outer casing 11 of the housing 10 such that a bottom end of the resilient member 30 abuts the collar 21 of the actuator 20 and a top end of the resilient member 30 abuts the bottom annular member 42 of the adapter 40. An interior of the adapter 40 does not communicate with the at least one through hole 321 of the column 32 because of the said top valve stem 37.

FIGS. 1 to 5 show a first embodiment of the leak proof needleless medical connector of the present invention.

The outer casing 11 of the housing 10 has an inner surface, an annular locking projection 112 and a plurality of spaced longitudinal locking ribs 113. The annular locking projection 112 and the longitudinal locking ribs 113 extend from the inner surface of the outer casing 11.

Figure 26:
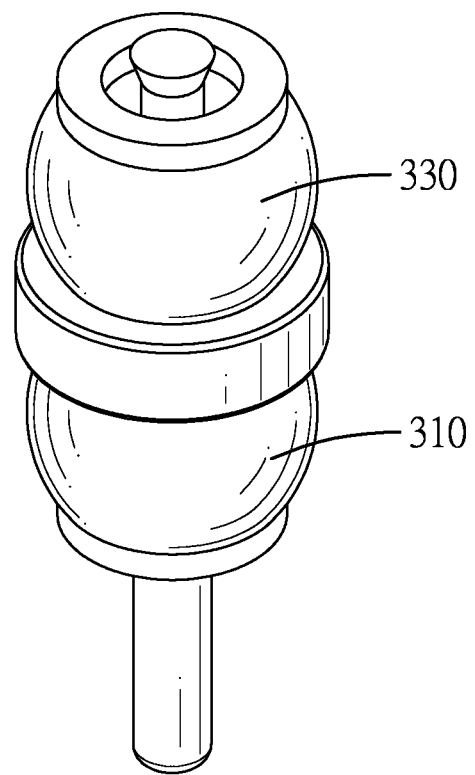
FIGS. 26 to 29 are enlarged perspective views of spherical compression tubes of the leak proof needleless medical connectors in accordance with the present invention.

The bottom valve stem 34 extends downward from a central portion of a bottom surface of the column 32. The top valve stem 37 extends upward from a central portion of a top surface of the column 32. The column 32 has a plurality of through holes 321 defined therethrough. The through holes 321 are spaced around the bottom valve stem 34 and the top valve stem 37. The bottom valve stem 34 has a flange 341 at its top end. The flange 341 is inserted into a top of the gap 36 such that the gap 36 does not communicate with the through holes 321 of the column 32. The top valve stem 37 has an enlarged portion 371 at its top end. The enlarged portion 371 abuts a bottom end of an inner surface of the bottom annular member 42 of the adapter 40 such that the interior of the upper compression tube 33 does not communicate with the interior of the adapter 40. Walls of the lower and upper compression tubes 31, 33 may be waved, or, with reference to FIG. 26, walls of the lower and upper compression tubes 310, 330 may be spherical.

The bottom annular member 42 of the adapter 40 has a bottom surface, an outer surface, a second annular receiving groove 421, an annular locking groove 422 and a plurality of spaced longitudinal locking channels 423. The second annular receiving groove 421 is formed in the bottom surface of the bottom annular member 42. The top end of the upper compression tube 33 is received in the second annular receiving groove 421. The annular locking groove 422 and the longitudinal locking channels 423 are formed in the outer surface of the bottom annular member 42. The annular locking projection 112 of the outer casing 11 of the housing 10 corresponds to and engages the annular locking groove 422 to prevent the adapter 40 from being removed from the housing 10. The longitudinal locking ribs 113 of the outer casing 11 of the housing 10 correspond to and engage the longitudinal locking channels 423 to prevent the adapter 40 from rotating relative to the housing 10.

In the first embodiment, the leak proof needleless medical connector comprises four components including the housing 10, the actuator 20, the resilient member 30 and the adapter 40. The lower compression tube 31, the column 32, the upper compression tube 33, the bottom valve stem 34 and the top valve stem 37 are integrally formed to construct the resilient member 30.

Figure 5:
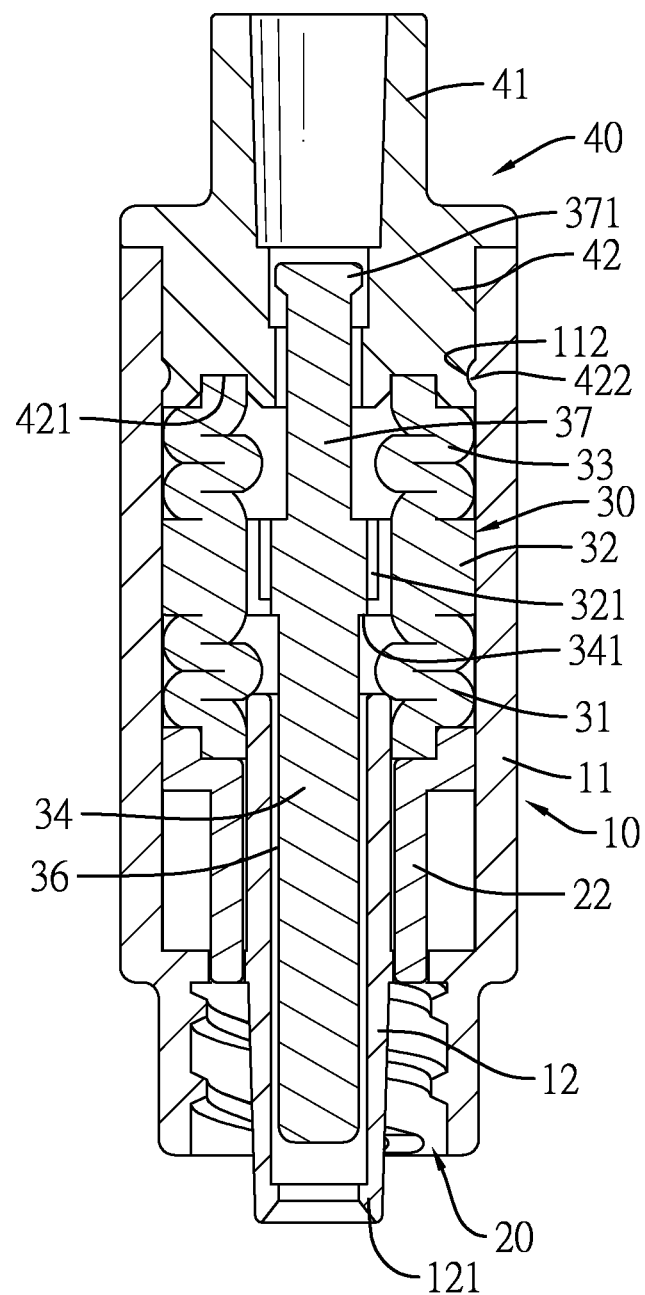
FIG. 5 is a cross-sectional side view of the leak proof needleless medical connector in FIG. 1 shown in an actuated state.
Figure 6:
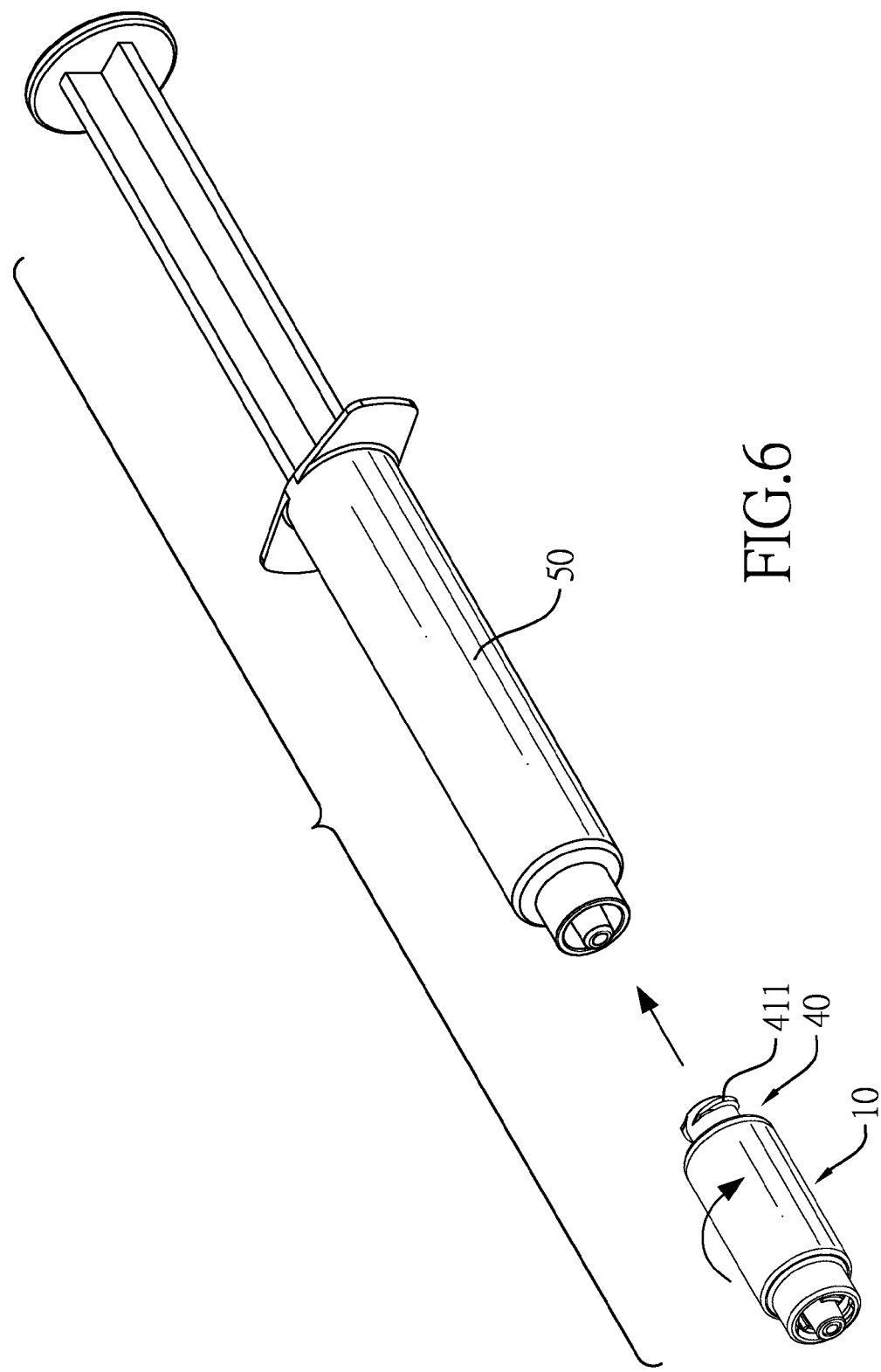
FIG. 6 is an operational perspective view of the leak proof needleless medical connector in FIG. 1 showing that the needleless medical connector is engaged with a needleless medical injector.
Figure 7:
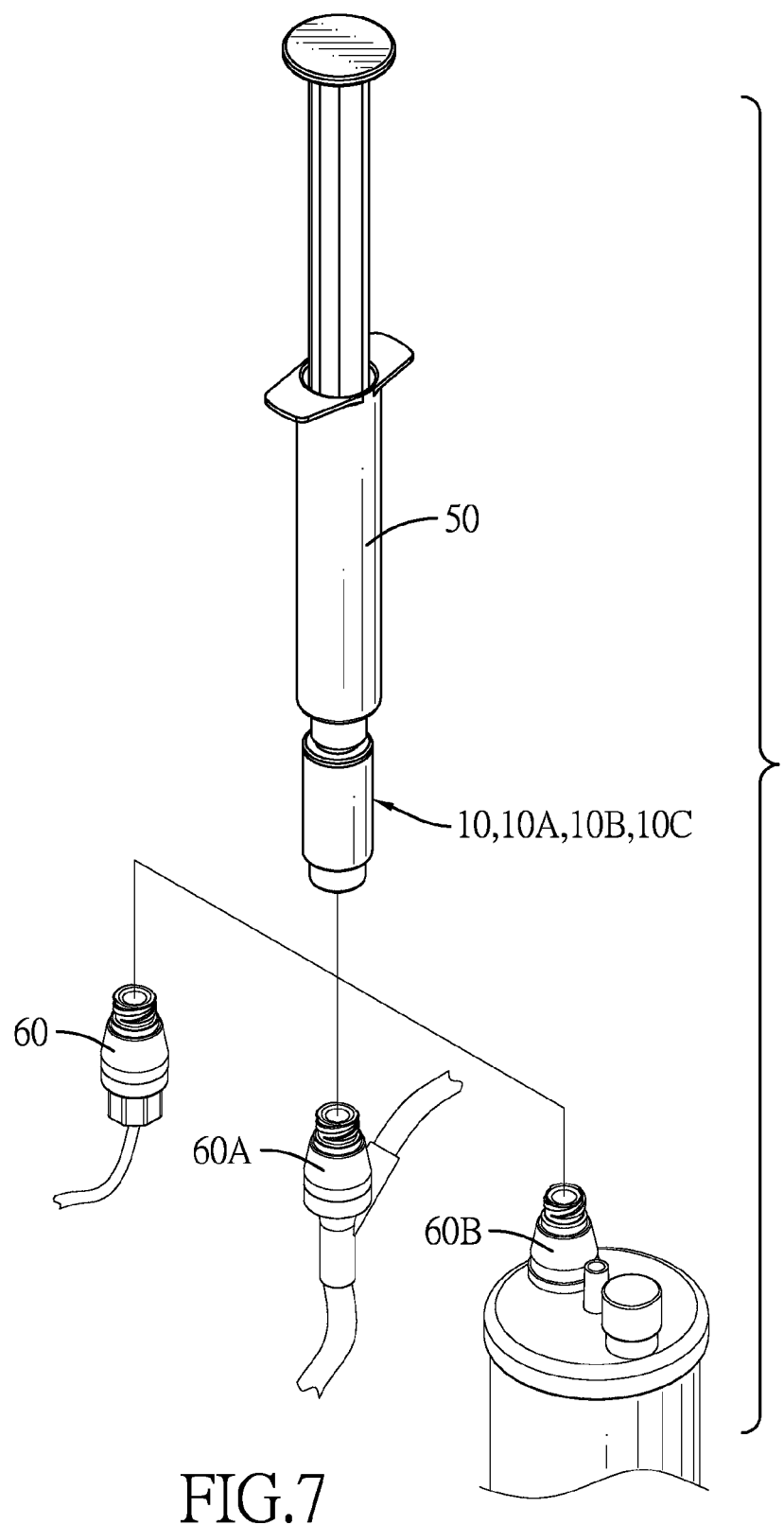
FIG. 7 is an operational perspective view of the leak proof needleless medical connector in FIG. 1 with the needleless medical injector, showing that the needleless medical connector is engaged with one of the dosing units.
Figure 8:
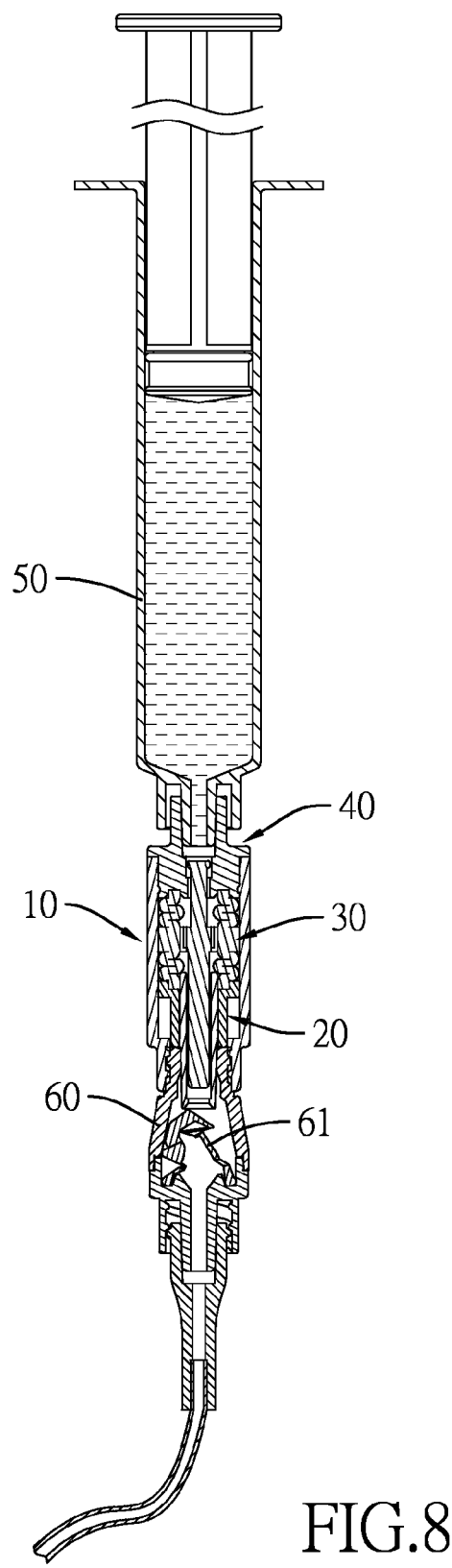
FIGS. 8 to 10 are operational cross-sectional side views of the leak proof needleless medical connector in FIG. 1 with the needleless medical injector and the dosing unit.

With reference to FIG. 6, when the first embodiment of the leak proof needleless medical connector is in use, the external threads 411 of the top annular member 41 of the adapter 40 are screwed into internal threads of a needleless medical injector 50. With reference to FIG. 7, external threads of an appropriate dosing unit 60, 60A, 60B are then screwed with the internal threads 111 of the outer casing 11 of the housing 10. The following description describes a situation in which the dosing unit 60 is used. With reference to FIGS. 5 and 8, the dosing unit 60 is screwed into the housing 10 to move the guide members 22 of the actuator 20 longitudinally within the housing 10, such that the actuator 20 is moved up to compress the lower and upper compression tubes 31, 33. Under this circumstance, the bottom end of the bottom valve stem 34 is moved away from the bottom annular blocking projection 121 of the valve tube 12 of the housing 10 to open the open bottom of the valve tube 12, the flange 341 of the bottom valve stem 34 is moved away from the top of the gap 36 to allow the gap 36 to communicate with the through holes 321 of the column 32, and the enlarged portion 371 of the top valve stem 37 does not abut the inner surface of the bottom annular member 42 of the adapter 40 to allow the interior of the upper compression tube 33 to communicate with the interior of the adapter 40.

Figure 9:
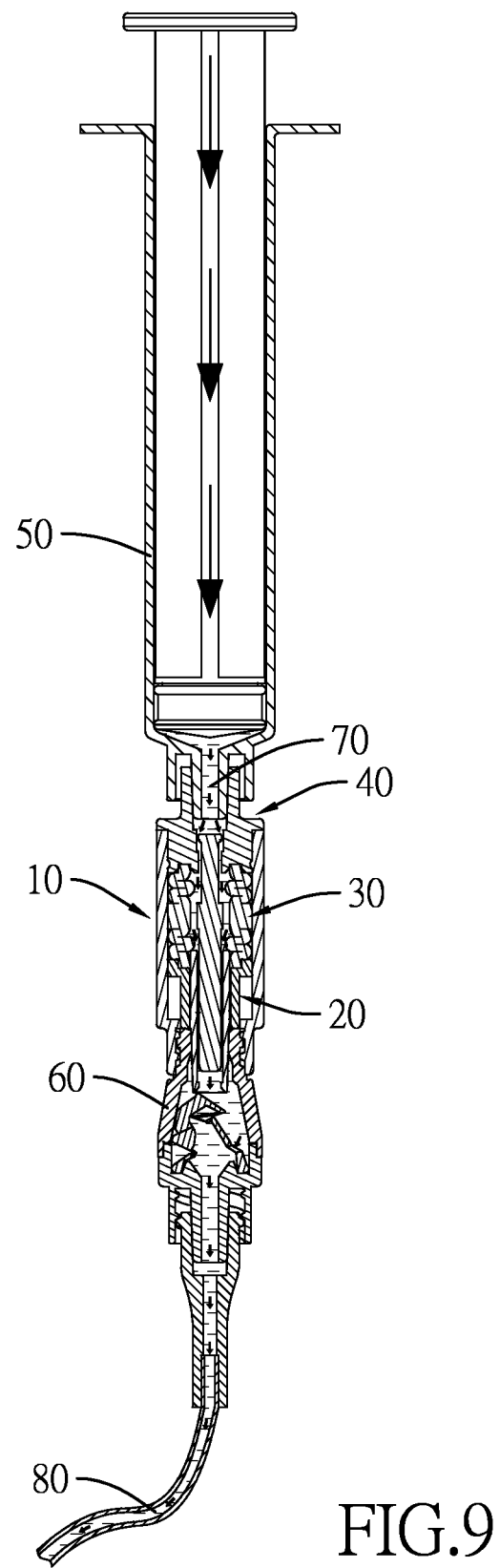

When the dosing unit 60 is screwed into the housing 10, the valve tube 12 of the housing 10 is inserted into the dosing unit 60 and compresses a resilient member 61 of the dosing unit 60. Thus, the open bottom of the valve tube 12 communicates with an interior of the dosing unit 60 and a flow channel is formed within the needleless medical connector and the dosing unit 60. With reference to FIG. 9, medication 70 in the needleless medical injector 50 flows in sequence through the needleless medical connector, the dosing unit 60, and a fluid infusion tube 80 connected to the dosing unit 60, and the medication 70 is then injected into a patient.

Figure 4:
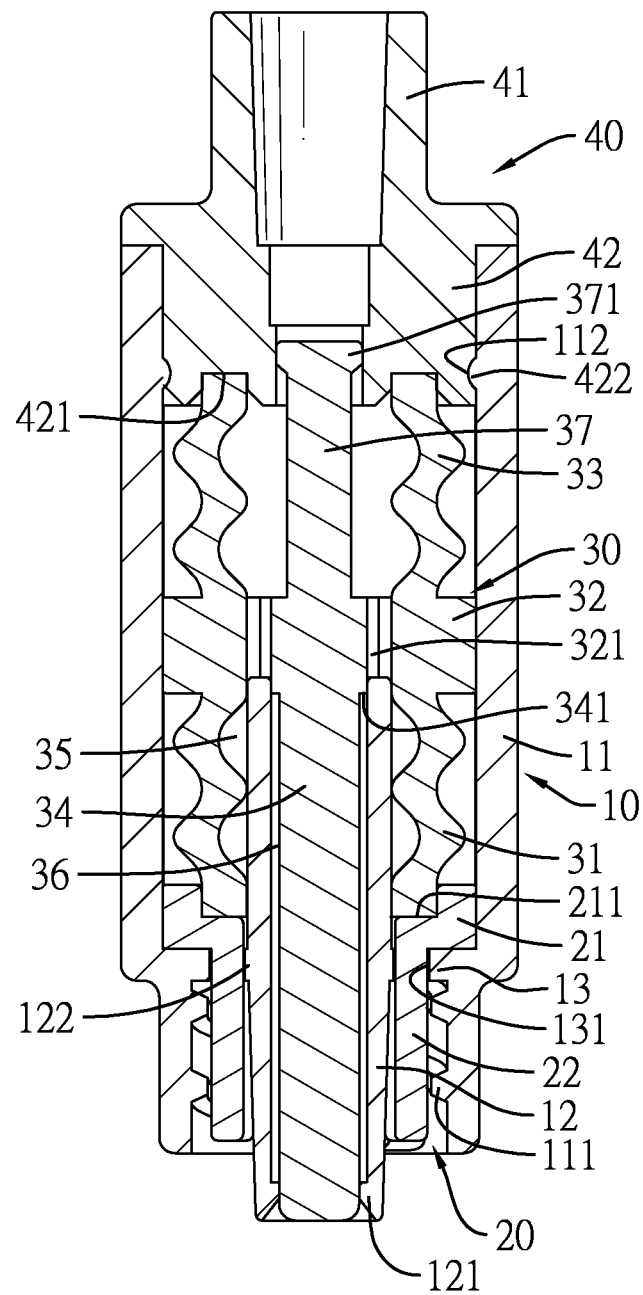
FIG. 4 is a cross-sectional side view of the leak proof needleless medical connector in FIG. 1.
Figure 10:
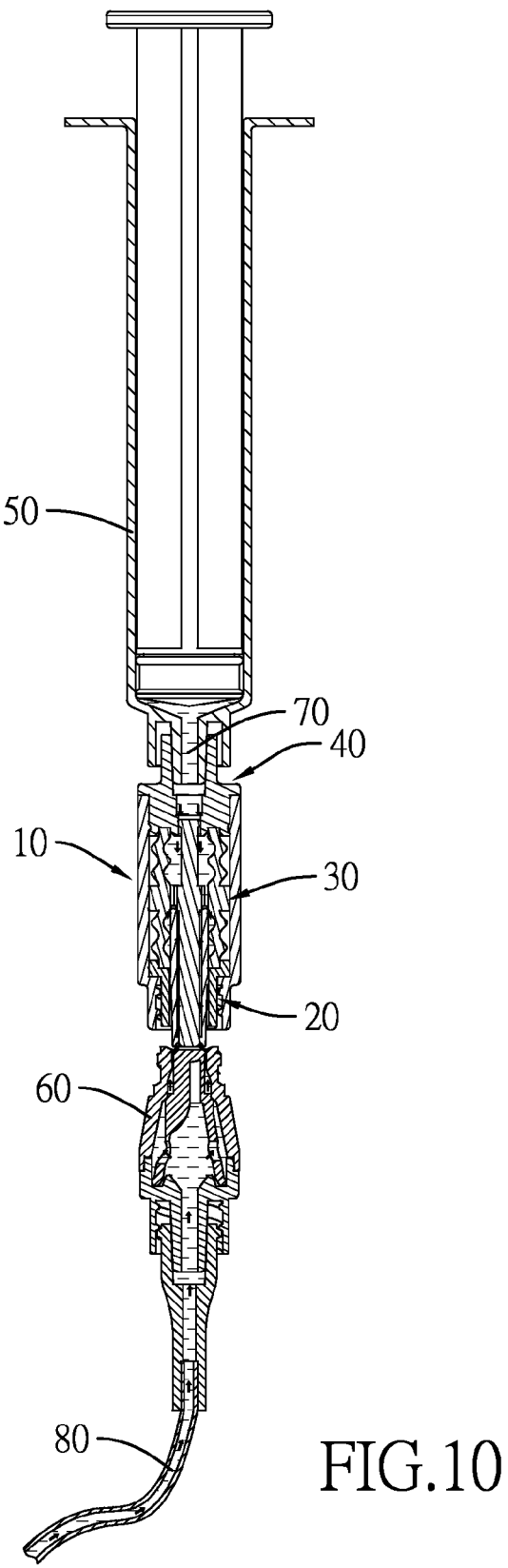
Figure 11:
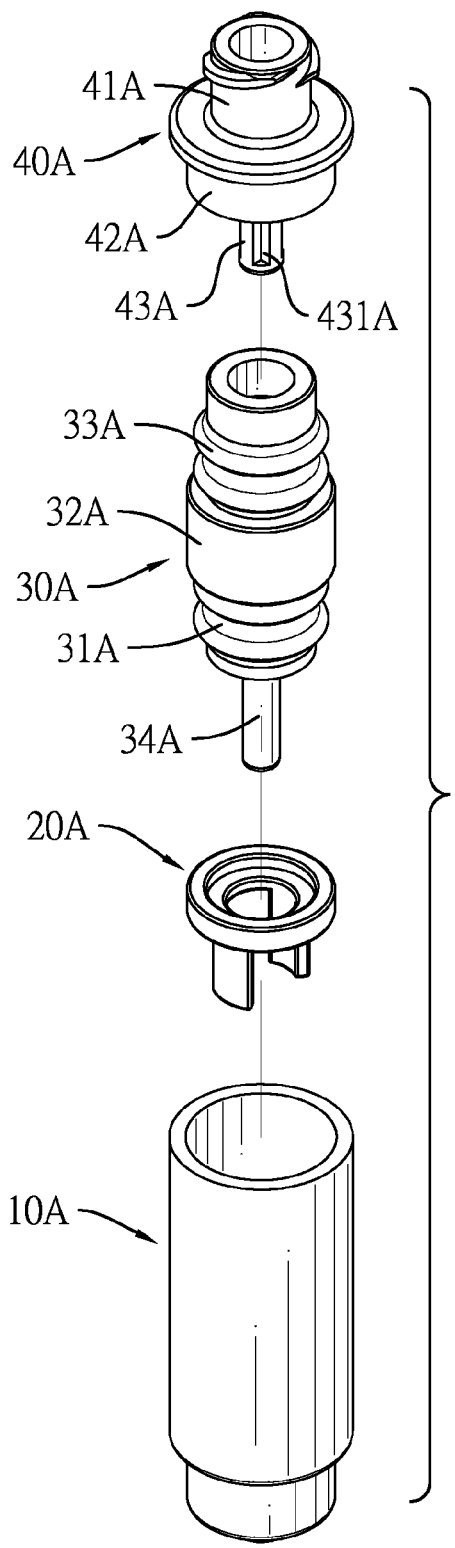
FIG. 11 is an exploded perspective view of a second embodiment of the leak proof needleless medical connector in accordance with the present invention.
Figure 12:
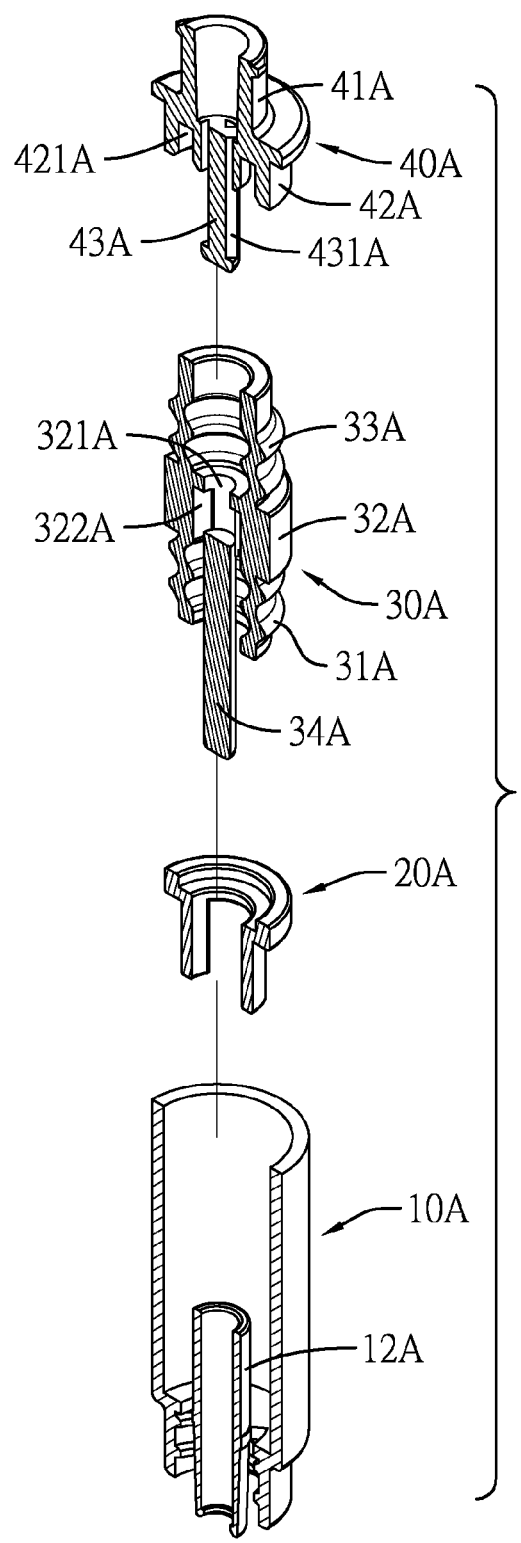
FIG. 12 is an exploded cross-sectional perspective view of the leak proof needleless medical connector in FIG. 11.

With reference to FIGS. 4 and 10, after the necessary medication has been dispensed, the dosing unit 60 is removed from the needleless medical connector. The lower and upper compression tubes 31, 33 extend themselves due to their resilience to produce three sealing effects as follows. Firstly, the bottom end of the bottom valve stem 34 returns to abut the bottom annular blocking projection 121 of the valve tube 12 of the housing 10 and to close the open bottom of the valve tube 12. Secondly, the flange 341 of the bottom valve stem 34 returns to be inserted into the top of the gap 36. Thirdly, the enlarged portion 371 of the top valve stem 37 returns to abut the inner surface of the bottom annular member 42 of the adapter 40. Therefore, the needleless medical connector has good sealing property to prevent leakage of the medication. In addition, the moment the dosing unit 60 is removed, a vacuum is formed in the needleless medical connector and draws the medication remaining on the external surface of the needleless medical connector into the needleless medical connector such that no medication residue exists outside the needleless medical connector.

FIGS. 11 to 14 show a second embodiment of the leak proof needleless medical connector of the present invention.

Figure 27:
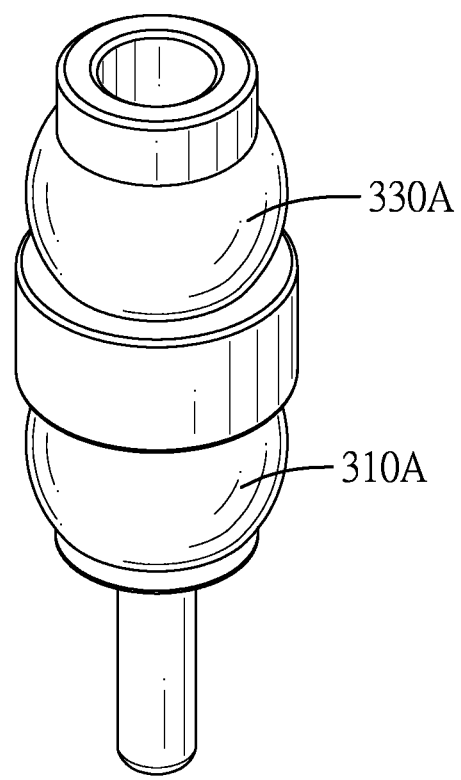

The column 32A has a through hole 321A extending through a central portion thereof. A top end of the bottom valve stem 34A is connected to a bottom end of an inner surface of the through hole 321A. A plurality of spaced longitudinal depressions 322A are formed in the inner surface of the through hole 321A. Each depression 322A has an open bottom communicating with the interior of the lower compression tube 31A and the gap 36A. Walls of the lower and upper compression tubes 31A, 33A may be waved, or, with reference to FIG. 27, walls of the lower and upper compression tubes 310A, 330A may be spherical.

The bottom annular member 42A of the adapter 40A has a bottom surface and a second annular receiving groove 421A. The second annular receiving groove 421A is formed in the bottom surface of the bottom annular member 42A. The top end of the upper compression tube 33A is received in the second annular receiving groove 421A. The top valve stem 43A extends downward from an interior of the bottom annular member 42A and has an outer surface and a plurality of spaced longitudinal channels 431A. The channels 431A are formed in the outer surface of the top valve stem 43A. Each channel 431A has an open top communicating with an interior of the top annular member 41A of the adapter 40A. A bottom end of the top valve stem 43A abuts a top end of the inner surface of the through hole 321A of the column 32A such that the interior of the upper compression tube 33A does not communicate with the through hole 321A of the column 32A.

In the second embodiment, the leak proof needleless medical connector comprises four components including the housing 10A, the actuator 20A, the resilient member 30A and the adapter 40A. The lower compression tube 31A, the column 32A, the upper compression tube 33A and the bottom valve stem 34A are integrally formed to construct the resilient member 30A. The top annular member 41A, the bottom annular member 42A and the top valve stem 43A are integrally formed to construct the adapter 40A.

Figure 14:
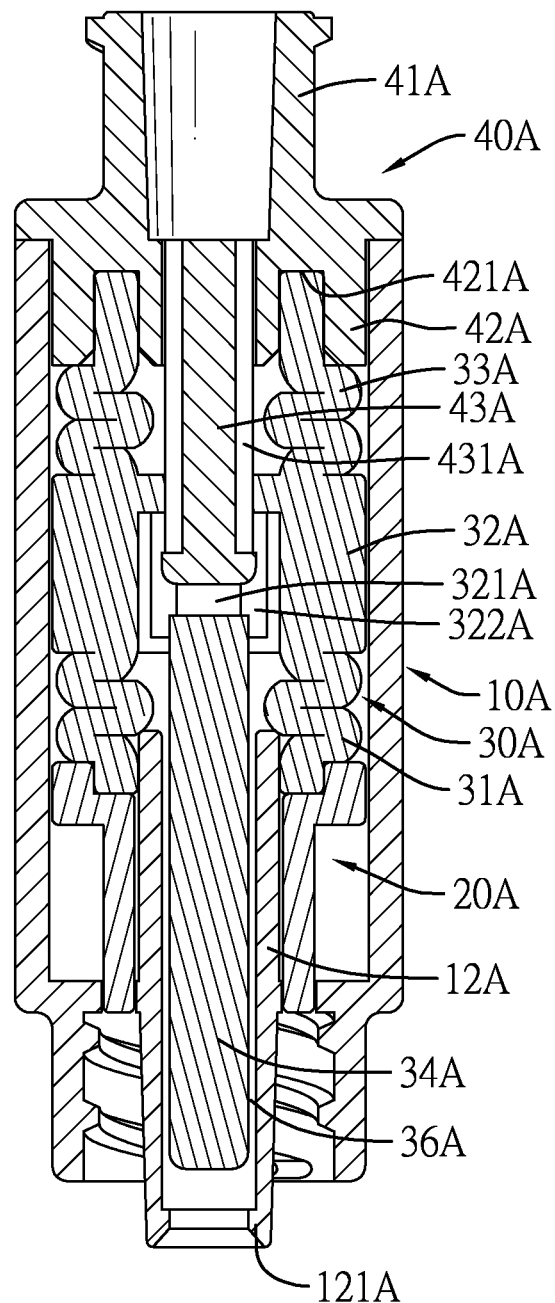
FIG. 14 is a cross-sectional side view of the leak proof needleless medical connector in FIG. 11 shown in an actuated state.
Figure 15:
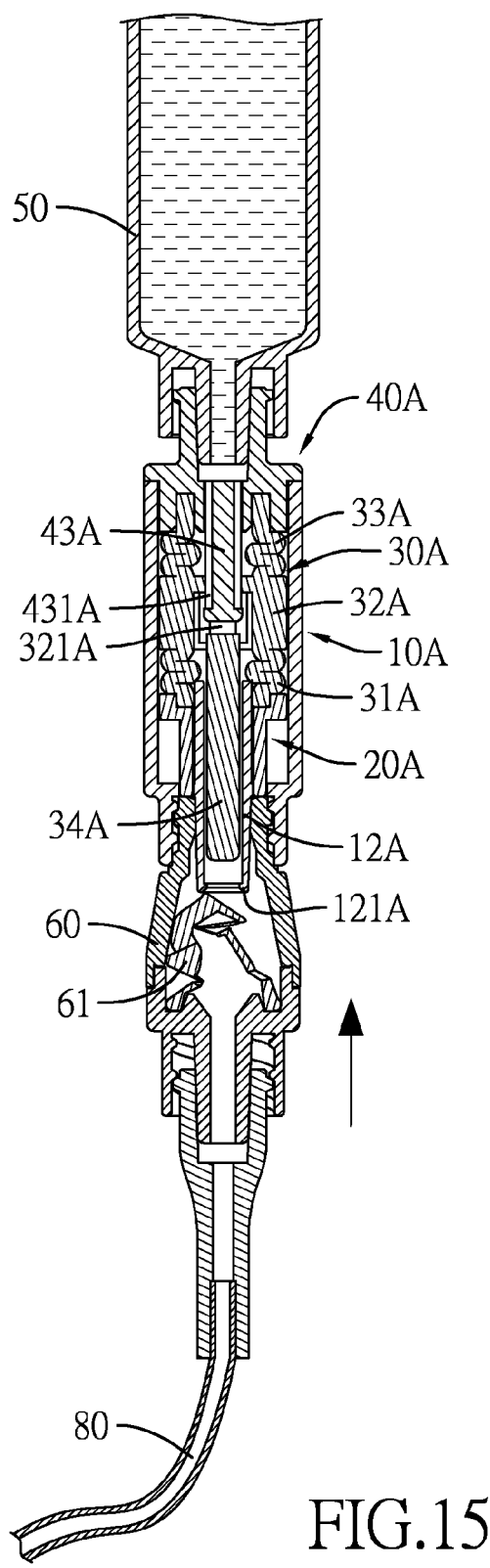
FIGS. 15 to 17 are operational cross-sectional side views of the leak proof needleless medical connector in FIG. 11 with a needleless medical injector and a dosing unit.
Figure 16:
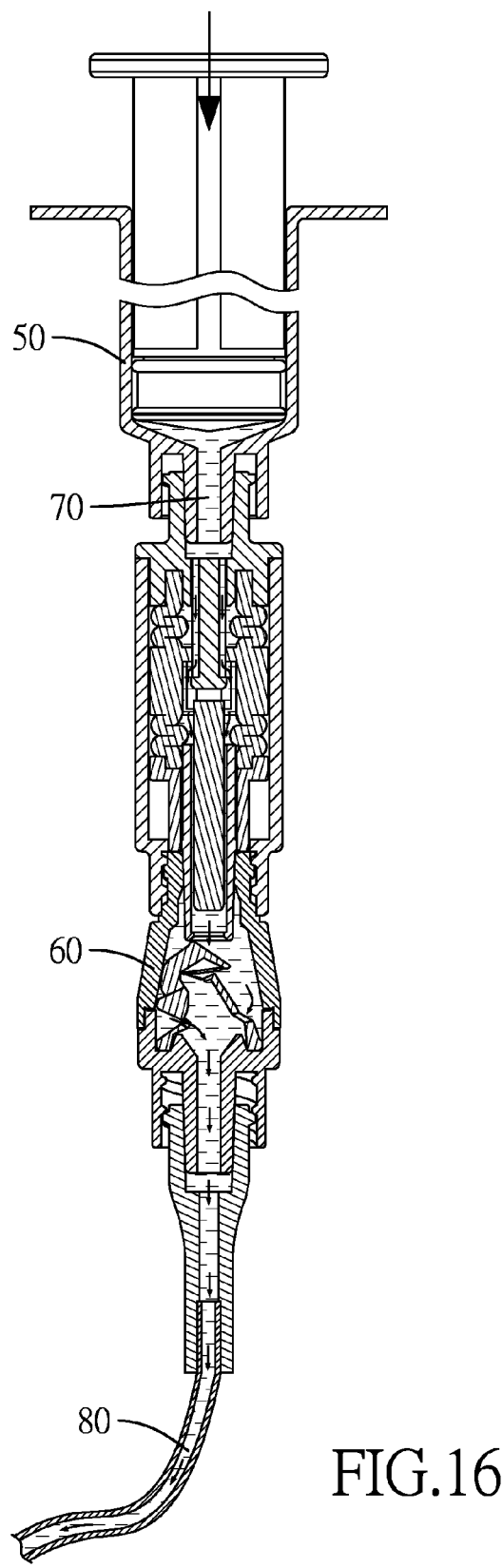

With reference to FIG. 7, when the second embodiment of the leak proof needleless medical connector is in use, the needleless medical connector is screwed into a needleless medical injector 50 and an appropriate dosing unit 60, 60A, 60B is then screwed into the needleless medical connector. The following description describes a situation in which the dosing unit 60 is used. With reference to FIGS. 14 and 15, the dosing unit 60 is screwed into the housing 10A to move the actuator 20A up and to compress the lower and upper compression tubes 31A, 33A. Under this circumstance, the bottom end of the bottom valve stem 34A is moved away from the bottom annular blocking projection 121A of the valve tube 12A of the housing 10A to open the open bottom of the valve tube 12A and to allow the open bottom of the valve tube 12A to communicate with an interior of the dosing unit 60, and the bottom end of the top valve stem 43A does not abut the inner surface of the through hole 321A of the column 32A to allow the interior of the upper compression tube 33A to communicate with the through hole 321A of the column 32A through the channels 431A of the top valve stem 43A. Thus, a flow channel is formed within the needleless medical connector and the dosing unit 60. With reference to FIG. 16, medication 70 in the needleless medical injector 50 flows in sequence through the needleless medical connector, the dosing unit 60, and a fluid infusion tube 80 connected to the dosing unit 60, and the medication is then injected into a patient.

Figure 13:
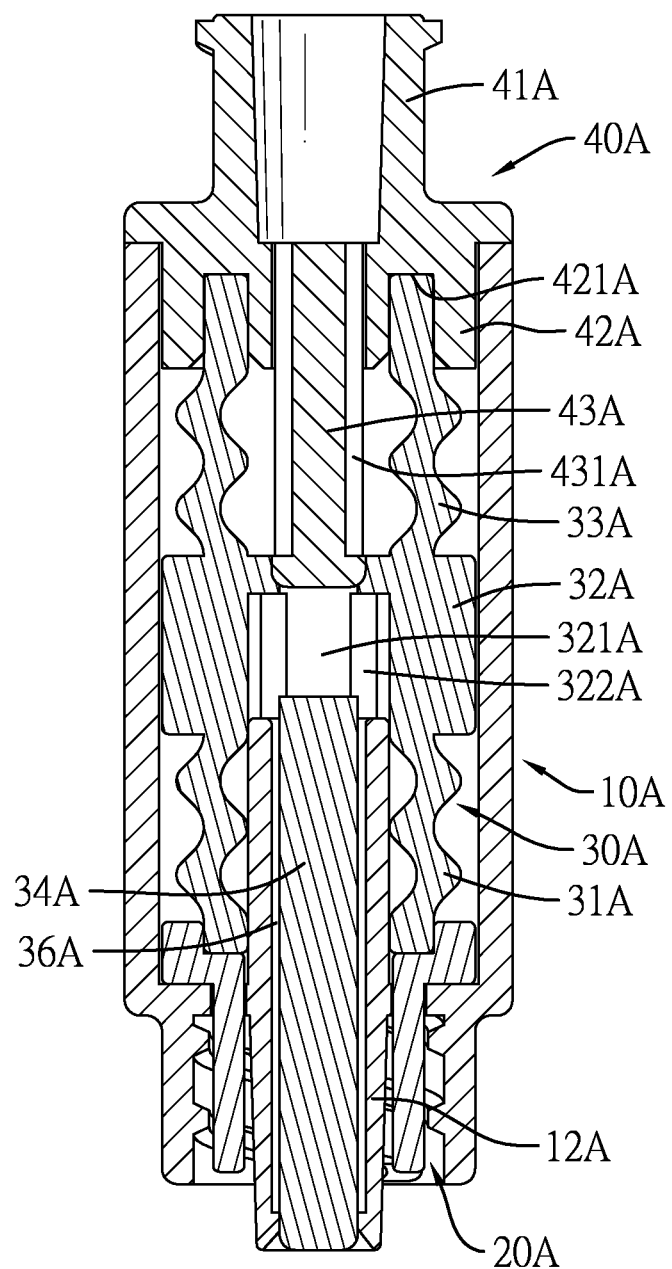
FIG. 13 is a cross-sectional side view of the leak proof needleless medical connector in FIG. 11.
Figure 17:
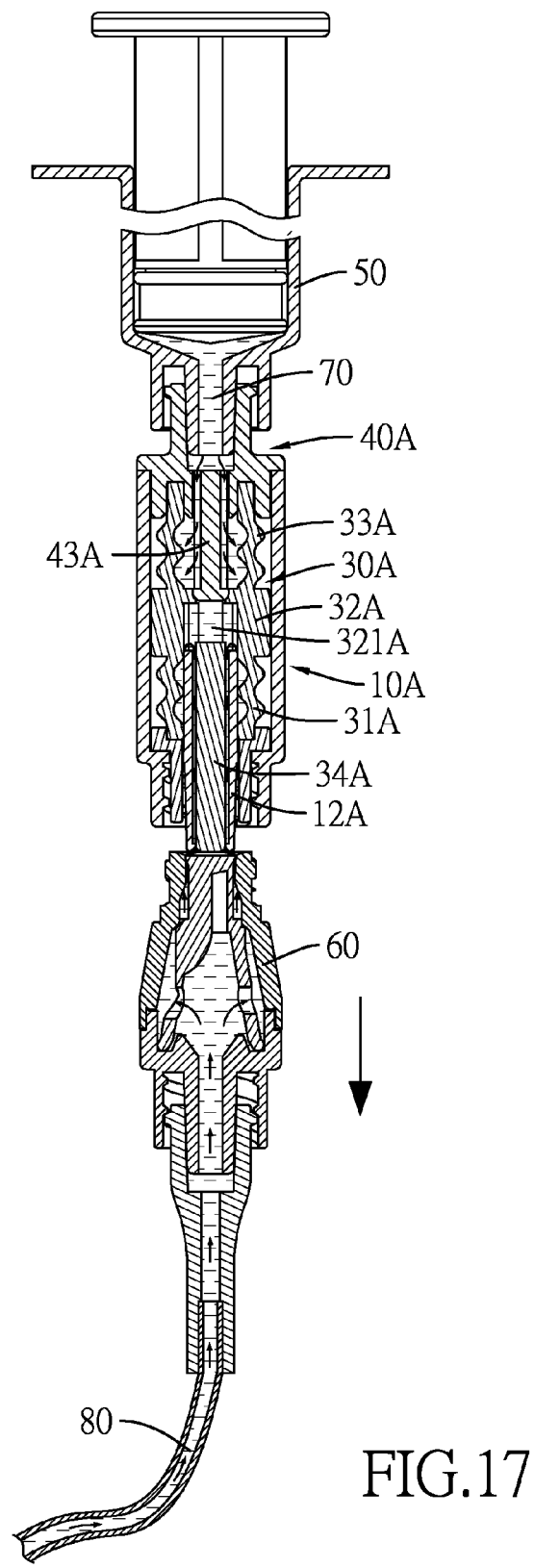
Figures 18, 19:
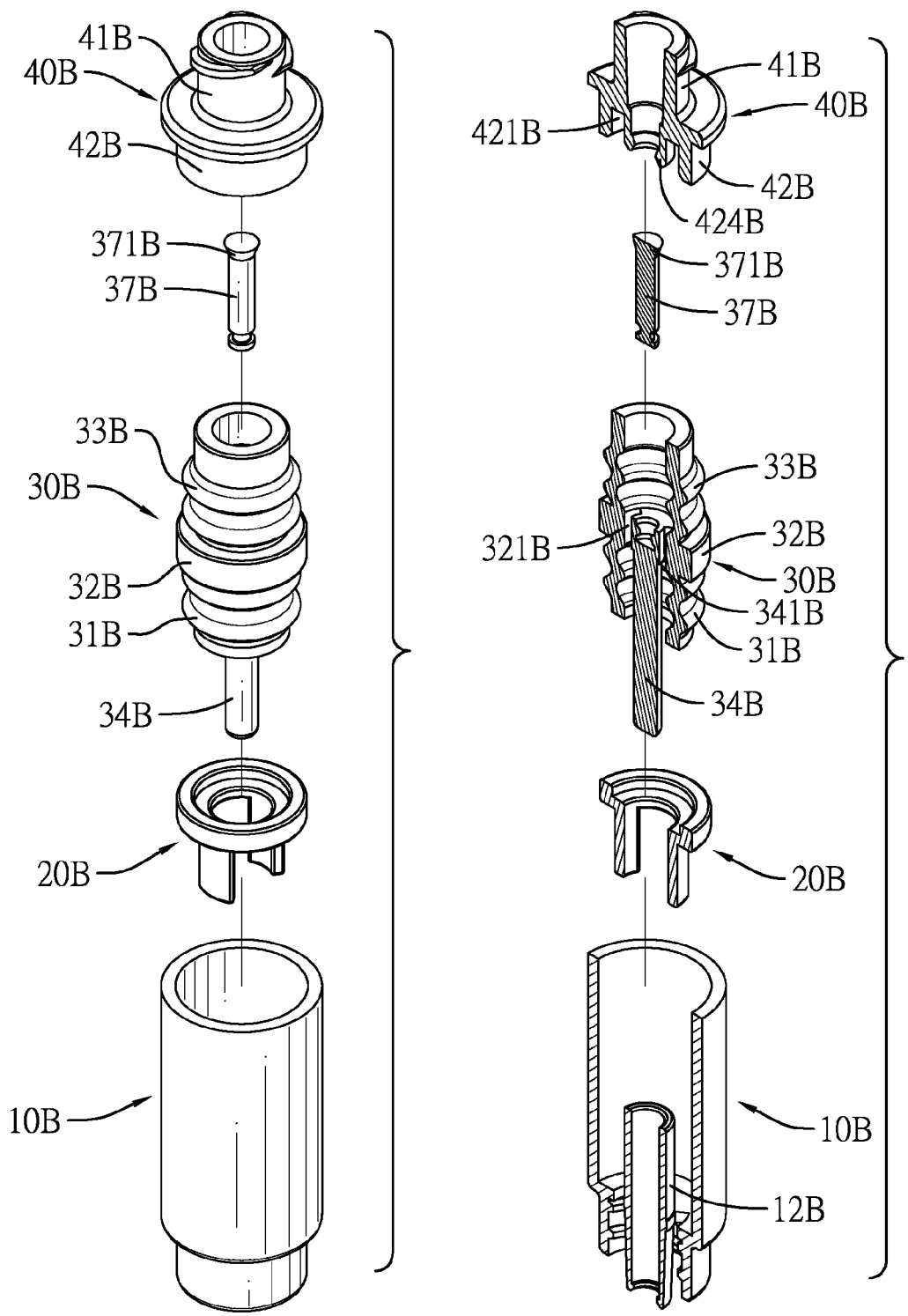
FIG. 18 is an exploded perspective view of a third embodiment of the leak proof needleless medical connector in accordance with the present invention.
FIG. 19 is an exploded cross-sectional perspective view of the leak proof needleless medical connector in FIG. 18.

With reference to FIGS. 13 and 17, after the necessary medication has been dispensed, the dosing unit 60 is removed from the needleless medical connector. The lower and upper compression tubes 31A, 33A extend themselves due to their resilience to produce three sealing effects as follows. Firstly, the bottom end of the bottom valve stem 34A returns to close the open bottom of the valve tube 12A of the housing 10A. Secondly, the top end of the inner surface of the lower compression tube 31A returns to abut the outer surface of the valve tube 12A. Thirdly, the bottom end of the top valve stem 43A of the adapter 40A returns to abut the inner surface of the through hole 321A of the column 32A. In addition, the moment the dosing unit 60 is removed, a vacuum is formed in the needleless medical connector. Therefore, the needleless medical connector has good sealing property to prevent leakage of the medication and no medication residue exists outside the needleless medical connector.

FIGS. 18 to 21 show a third embodiment of the leak proof needleless medical connector of the present invention.

Figure 28:
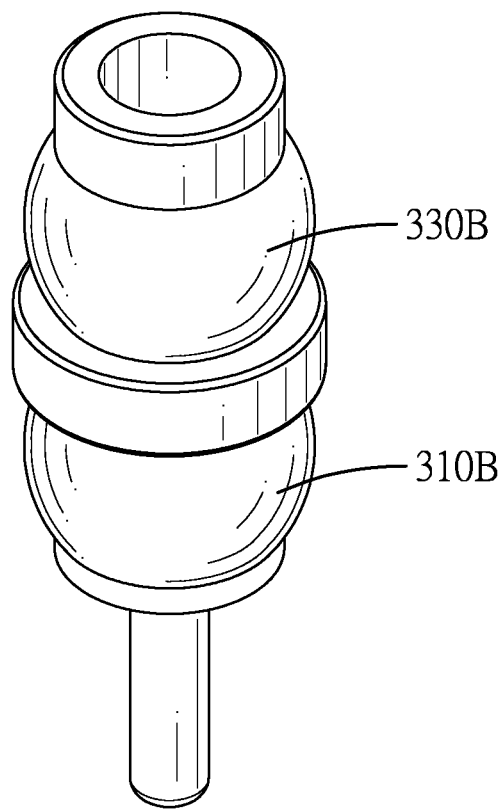

The bottom valve stem 34B extends downward from a central portion of a bottom surface of the column 32B. The column 32B has a plurality of through holes 321B therethrough. The through holes 321B are spaced around the bottom valve stem 34B. The bottom valve stem 34B has a flange 341B at its top end. The flange 341B is inserted into a top of the gap 36B such that the gap 36B does not communicate with the through holes 321B of the column 32B. The top valve stem 37B is mounted upward from a central portion of a top surface of the column 32B. The top valve stem 37B has an enlarged portion 371B at its top end. Walls of the lower and upper compression tubes 31B, 33B may be waved, or, with reference to FIG. 28, walls of the lower and upper compression tubes 310B, 330B may be spherical.

The bottom annular member 42B of the adapter 40B has a bottom surface, an inner surface, a second annular receiving groove 421B and a top annular blocking projection 424B. The second annular receiving groove 421B is formed in the bottom surface of the bottom annular member 42B. The top end of the upper compression tube 33B is received in the second annular receiving groove 421B. The top annular blocking projection 424B extends from a bottom end of the inner surface of the bottom annular member 42B. The enlarged portion 371B of the top valve stem 37B abuts the top annular blocking projection 424B such that the interior of the upper compression tube 33B does not communicate with the interior of the adapter 40B.

In the third embodiment, the leak proof needleless medical connector comprises five components including the housing 10B, the actuator 20B, the resilient member 30B, the top valve stem 37B and the adapter 40B. The lower compression tube 31B, the column 32B, the upper compression tube 33B and the bottom valve stem 34B are integrally formed to construct the resilient member 30B.

Figure 21:
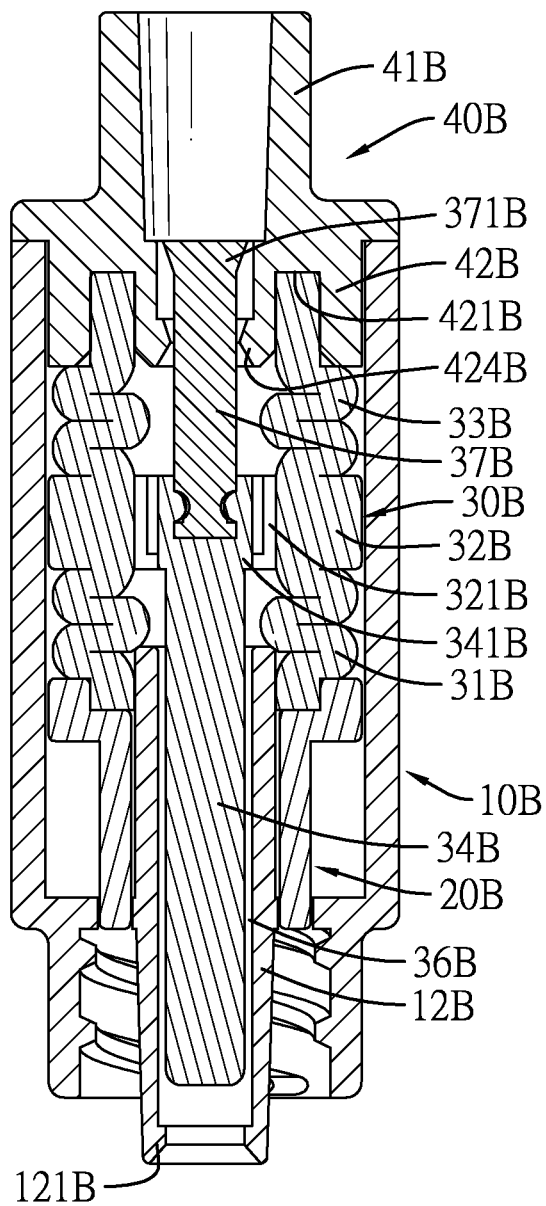
FIG. 21 is a cross-sectional side view of the leak proof needleless medical connector in FIG. 18 shown in an actuated state.
Figure 22:
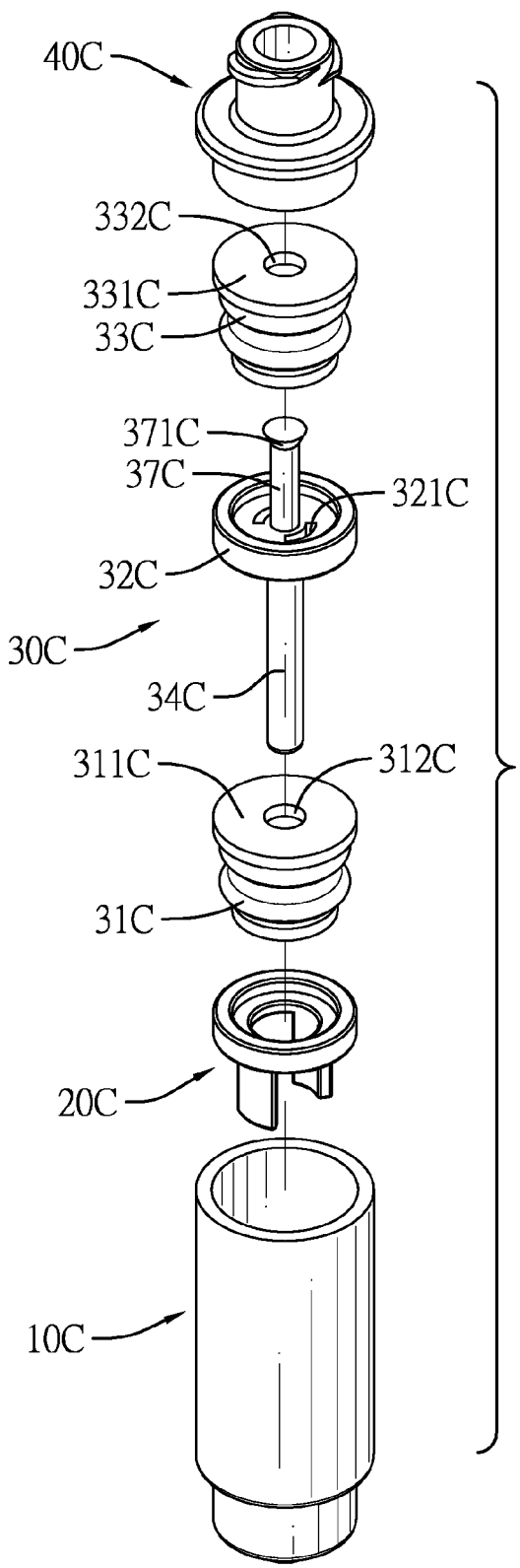
FIG. 22 is an exploded perspective view of a fourth embodiment of the leak proof needleless medical connector in accordance with the present invention.
Figure 23:
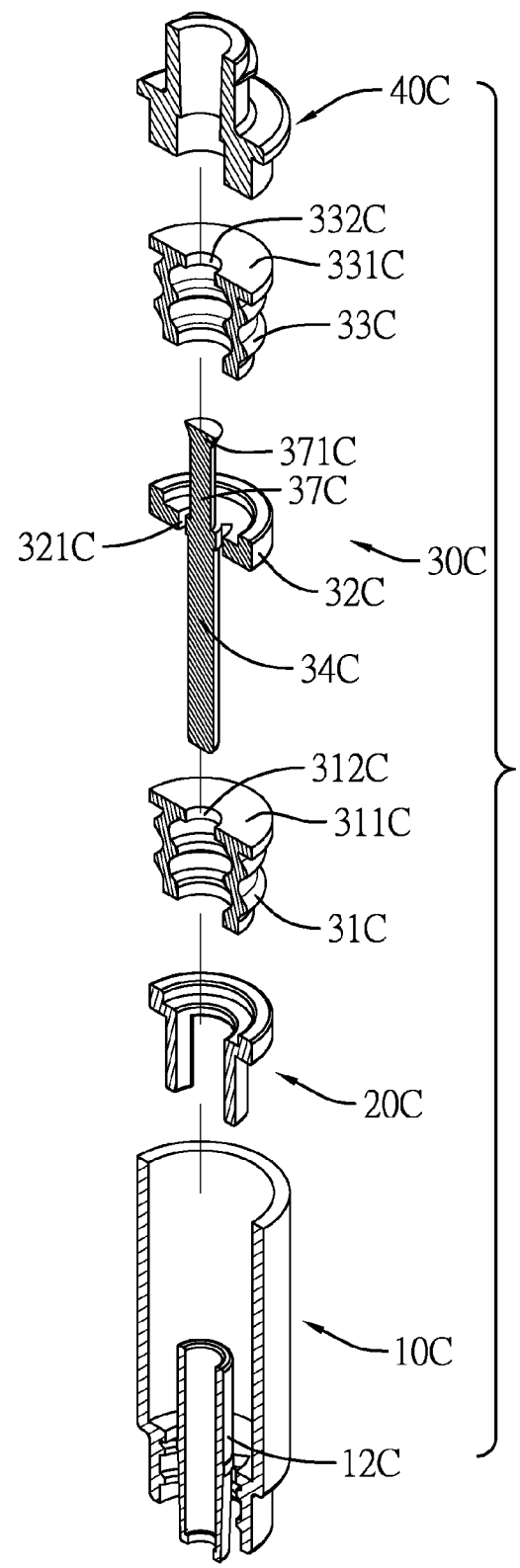
FIG. 23 is an exploded cross-sectional perspective view of the leak proof needleless medical connector in FIG. 22.

With reference to FIG. 7, when the third embodiment of the leak proof needleless medical connector is in use, the needleless medical connector is screwed into a needleless medical injector 50 and an appropriate dosing unit 60, 60A, 60B is then screwed into the needleless medical connector. The following description describes a situation in which the dosing unit 60 is used. With further reference to FIG. 21, the dosing unit 60 is screwed into the housing 10B to move the actuator 20B up and to compress the lower and upper compression tubes 31B, 33B. Under this circumstance, the bottom end of the bottom valve stem 34B is moved away from the bottom annular blocking projection 121B of the valve tube 12B of the housing 10B to open the open bottom of the valve tube 12B and to allow the open bottom of the valve tube 12B to communicate with an interior of the dosing unit 60, the flange 341B of the bottom valve stem 34B is moved away from the top of the gap 36B to allow the gap 36B to communicate with the through holes 321B of the column 32B, and the enlarged portion 371B of the top valve stem 37B is moved away from the top annular blocking projection 424B of the bottom annular member 42B of the adapter 40B to allow the interior of the upper compression tube 33B to communicate with the interior of the adapter 40B. Thus, a flow channel is formed within the needleless medical connector and the dosing unit 60 to allow passage of medication and injection of the medication into a patient.

Figure 20:
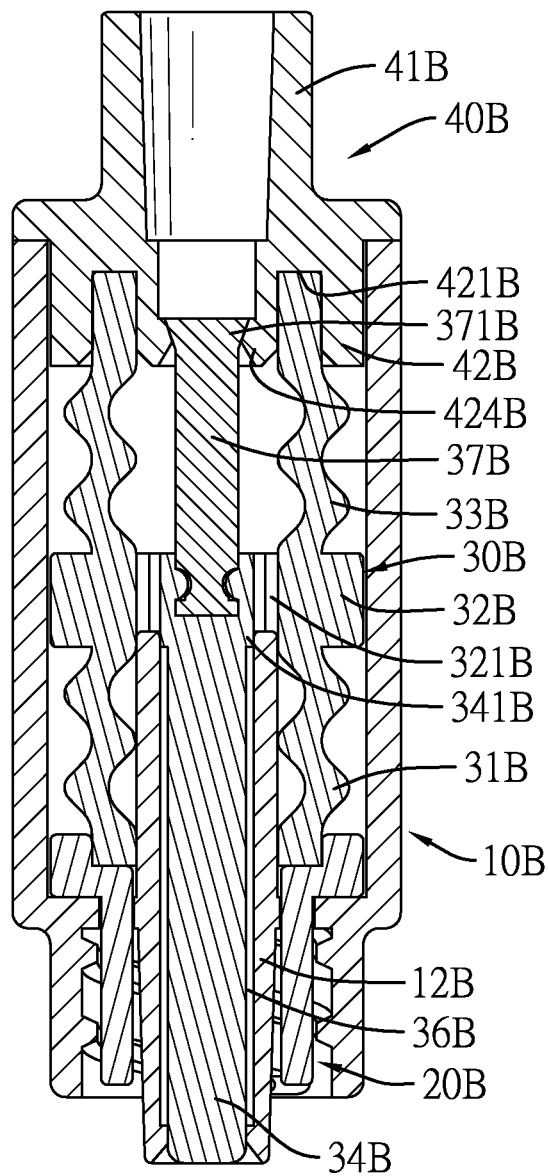
FIG. 20 is a cross-sectional side view of the leak proof needleless medical connector in FIG. 18.

With reference to FIG. 20, after the necessary medication has been dispensed, the dosing unit 60 is removed from the needleless medical connector. The lower and upper compression tubes 31B, 33B extend themselves due to their resilience to produce three sealing effects as follows. Firstly, the bottom end of the bottom valve stem 34B returns to close the open bottom of the valve tube 12B of the housing 10B. Secondly, the flange 341B of the bottom valve stem 34B returns to be inserted into the top of the gap 36B. Thirdly, the enlarged portion 371B of the top valve stem 37B returns to abut the top annular blocking projection 424B of the bottom annular member 42B of the adapter 40B. In addition, the moment the dosing unit 60 is removed, a vacuum is formed in the needleless medical connector. Therefore, the needleless medical connector has good sealing property to prevent leakage of the medication and no medication residue exists outside the needleless medical connector.

FIGS. 22 to 25 show a fourth embodiment of the leak proof needleless medical connector of the present invention.

Figure 29:
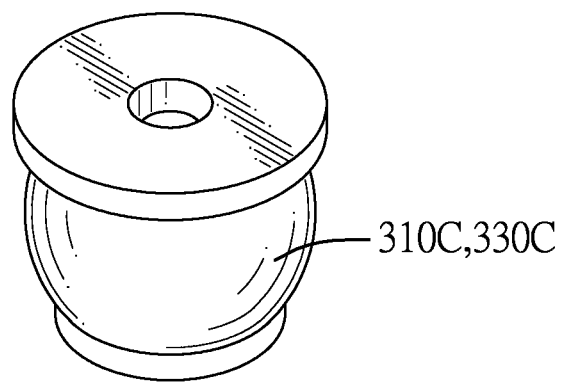

The lower compression tube 31C is mounted between the actuator 20C and the column 32C and has a lower top plate 311C and a lower central hole 312C. The lower central hole 312C extends through the lower top plate 311C. The upper compression tube 33C is mounted between the column 32C and the adapter 40C and has an upper top plate 331C and an upper central hole 332C. The upper central hole 332C extends through the upper top plate 331C. The bottom valve stem 34C extends downward from a central portion of a bottom surface of the column 32C. The top valve stem 37C extends upward from a central portion of a top surface of the column 32C. The column 32C has a plurality of through holes 321C therethrough. The through holes 321C are spaced around the bottom valve stem 34C and the top valve stem 37C. A top of the valve tube 12C of the housing 10C abuts a bottom surface of the lower top plate 311C of the lower compression tube 31C to urge the lower top plate 311C toward the column 32C to close open bottoms of the through holes 321C of the column 32C such that the through holes 321C do not communicate with the gap 36C. The top valve stem 37C has an enlarged portion 371C at its top end. The enlarged portion 371C abuts an inner surface of the upper central hole 332C of the upper compression tube 33C such that the interior of the upper compression tube 33C does not communicate with the interior of the adapter 40C. Walls of the lower and upper compression tubes 31C, 33C may be waved, or, with reference to FIG. 29, walls of the lower and upper compression tubes 310C, 330C may be spherical.

In the fourth embodiment, the leak proof needleless medical connector comprises six components including the housing 10C, the actuator 20C, the lower compression tube 31C, the column 32C, the upper compression tube 33C and the adapter 40C. The bottom valve stem 34C and the top valve stem 37C are integrally formed on the column 32C.

Figure 25:
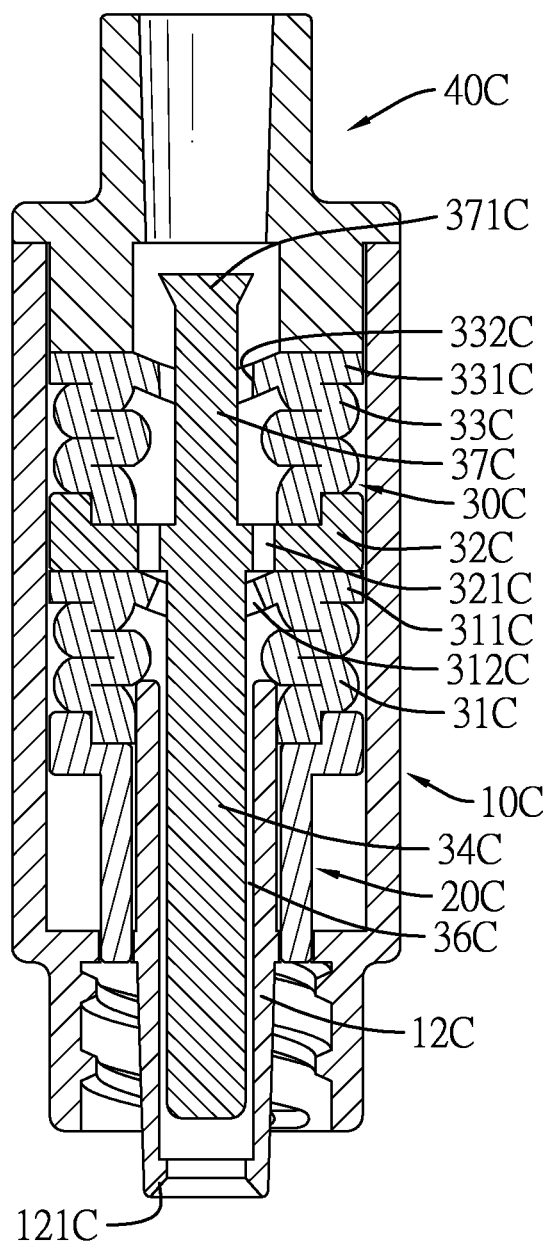
FIG. 25 is a cross-sectional side view of the leak proof needleless medical connector in FIG. 22 shown in an actuated state.

With reference to FIG. 7, when the fourth embodiment of the leak proof needleless medical connector is in use, the needleless medical connector is screwed into a needleless medical injector 50 and an appropriate dosing unit 60, 60A, 60B is then screwed into the needleless medical connector. The following description describes a situation in which the dosing unit 60 is used. With further reference to FIG. 25, the dosing unit 60 is screwed into the housing 10C to move the actuator 20C up and to compress the lower and upper compression tubes 31C, 33C. Under this circumstance, the bottom end of the bottom valve stem 34C is moved away from the bottom annular blocking projection 121C of the valve tube 12C of the housing 10C to open the open bottom of the valve tube 12C and to allow the open bottom of the valve tube 12C to communicate with an interior of the dosing unit 60, the top of the valve tube 12C does not abut the lower top plate 311C of the lower compression tube 31C to allow the gap 36C to communicate with the through holes 321C of the column 32C through the lower central hole 312C of the lower compression tube 31C, and the enlarged portion 371C of the top valve stem 37C does not abut the inner surface of the upper central hole 332C of the upper compression tube 33C to allow the interior of the upper compression tube 33C to communicate with the interior of the adapter 40C. Thus, a flow channel is formed within the needleless medical connector and the dosing unit 60 to allow passage of medication and injection of the medication into a patient.

Figure 24:
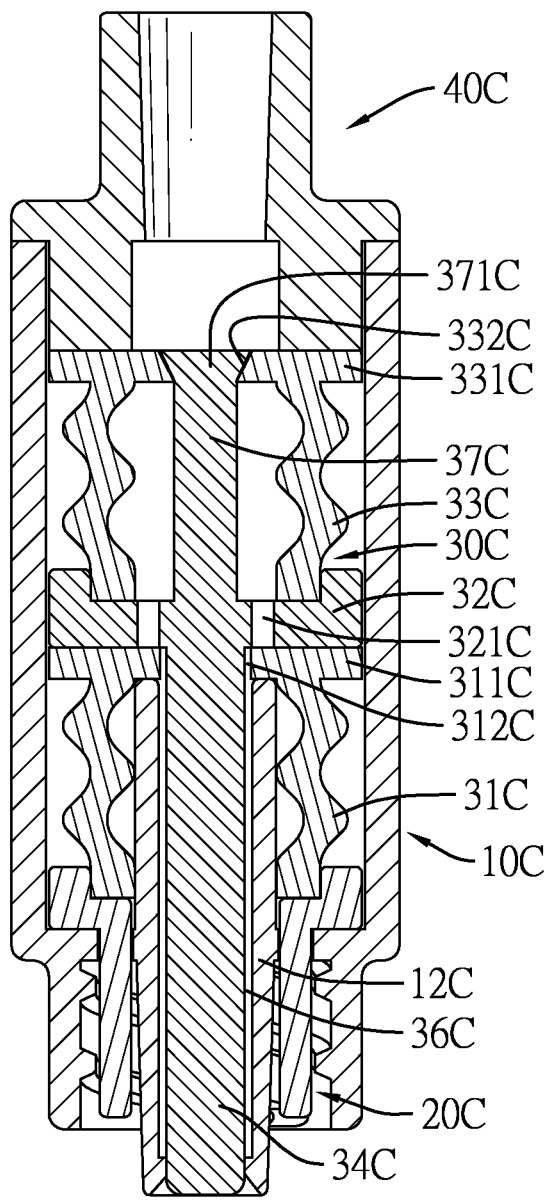
FIG. 24 is a cross-sectional side view of the leak proof needleless medical connector in FIG. 22.

With reference to FIG. 24, after the necessary medication has been dispensed, the dosing unit 60 is removed from the needleless medical connector. The lower and upper compression tubes 31C, 33C extend themselves due to their resilience to produce three sealing effects as follows. Firstly, the bottom end of the bottom valve stem 34C returns to close the open bottom of the valve tube 12C of the housing 10C. Secondly, the top of the valve tube 12C returns to abut the lower top plate 311C of the lower compression tube 31C. Thirdly, the enlarged portion 371C of the top valve stem 37C returns to abut the inner surface of the upper central hole 332C of the upper compression tube 33C. In addition, the moment the dosing unit 60 is removed, a vacuum is formed in the needleless medical connector. Therefore, the needleless medical connector has good sealing property to prevent leakage of the medication and no medication residue exists outside the needleless medical connector.

Even though numerous characteristics and advantages of the present invention have been set forth in the foregoing description, together with details of the structure and features of the invention, the disclosure is illustrative only. Changes may be made in the details, especially in matters of shape, size and arrangement of parts within the principles of the invention to the full extent indicated by the broad general meaning of the terms in which the appended claims are expressed.

What is claimed is:

1. A leak proof needleless medical connector comprising:
   a housing including:
      an outer casing; and
      a valve tube disposed within the outer casing and having:
         an inner surface; and
         a bottom annular blocking projection extending from a bottom end of the inner surface of the valve tube;
   an actuator being hollow, movably disposed within the outer casing of the housing and mounted around the valve tube of the housing;
   a resilient member disposed within the outer casing of the housing and including in sequence:
      a lower compression tube being resiliently compressible and expansible and mounted around the valve tube of the housing;
      a column having at least one through hole defined therethrough; and
      an upper compression tube being resiliently compressible and expansible, and an interior of the upper compression tube communicating with an interior of the lower compression tube through the at least one through hole of the column;
   a bottom valve stem disposed in the lower compression tube and mounted in the valve tube of the housing, a gap formed between the bottom valve stem and the valve tube, a top end of the valve tube selectively abutting the at least one through hole of the column such that the gap does not communicate with the interior of the upper compression tube, a bottom end of the bottom valve stem abutting the bottom annular blocking projection of the valve tube to close an open bottom of the valve tube;
   a top valve stem disposed in the upper compression tube and having an enlarged portion at its top end; and
   an adapter being hollow and mounted on a top of the outer casing of the housing, the resilient member mounted between the adapter and the actuator, the enlarged portion of the top valve stem selectively abutting an inner surface of the adapter such that the interior of the upper compression tube does not communicate with an interior of the adapter;

wherein, a needleless medical injector is screwed with the adapter to inject medication; before a dosing unit is mounted in the adapter, the enlarged portion of the top valve stem abuts the inner surface of the adapter to prevent the interior of the adapter from communicating with the interior of the upper compression tube, the top end of the valve tube abuts and seals the at least one through hole of the column to prevent the medication in the interior of the upper compression tube from flowing into the interior of the lower compression tube, and the bottom annular blocking projection of the valve tube abuts the bottom valve stem to prevent the medication in the valve tube of the housing from leaking out;

when the dosing unit is mounted in the outer casing of the housing to push upward the resilient member, the bottom valve stem is removed from the bottom annular blocking projection of the valve tube, the at least one through hole of the column is removed from the top end of the valve tube, and the enlarged portion of the top valve stem is removed from the inner surface of the adapter, thus the gap communicates with an exterior environment, the interior of the lower compression tube communicates with the interior of the upper compression tube, and the interior of the upper compression tube communicates with the interior of the adapter, so the medication in the adapter in sequence flows into the housing, the at least one through hole, and the gap, and then flows out between the bottom valve stem and the bottom annular blocking projection of the valve tube into the dosing unit.

2. The leak proof needleless medical connector as claimed in claim 1, wherein
   the housing includes an annular portion formed between the outer casing and the valve tube and having a plurality of guide holes defined through the annular portion; and
   the actuator includes
      a collar having a bottom surface; and
      a plurality of guide members extending downward from the bottom surface of the collar and corresponding to and inserted respectively through the guide holes of the annular portion of the housing.

3. The leak proof needleless medical connector as claimed in claim 2, wherein the adapter includes
   a top annular member; and
   a bottom annular member inserted into the top of the outer casing of the housing.

4. The leak proof needleless medical connector as claimed in claim 3, wherein the bottom valve stem extends downward from a bottom surface of the column, the top valve stem extends upward from a top surface of the column, the column has a plurality of through holes defined therethrough, the through holes are spaced around the bottom valve stem and the top valve stem, the bottom valve stem has a flange at its top end, the flange is inserted into a top of the gap such that the gap does not communicate with the through holes of the column, and the enlarged portion abuts an inner surface of the bottom annular member of the adapter.

5. The leak proof needleless medical connector as claimed in claim 4 comprising four components including the housing, the actuator, the resilient member and the adapter, wherein the lower compression tube, the column, the upper compression tube, the bottom valve stem and the top valve stem are integrally formed to construct the resilient member.

6. The leak proof needleless medical connector as claimed in claim 5, wherein the outer casing of the housing has
an inner surface; and
an annular locking projection and a plurality of spaced longitudinal locking ribs extending from the inner surface of the outer casing; and the bottom annular member of the adapter has
an outer surface; and
an annular locking groove and a plurality of spaced longitudinal locking channels formed in the outer surface of the bottom annular member, the annular locking projection of the outer casing of the housing corresponding to and engaging the annular locking groove, and the longitudinal locking ribs of the outer casing of the housing corresponding to and engaging the longitudinal locking channels.

7. A leak proof needleless medical connector comprising:
a housing including:
an outer casing; and
a valve tube disposed within the outer casing and having:
an inner surface; and
a bottom annular blocking projection extending from a bottom end of the inner surface of the valve tube;

an actuator being hollow, movably disposed within the outer casing of the housing and mounted around the valve tube of the housing;

a resilient member disposed within the outer casing of the housing and including in sequence:
a lower compression tube being resiliently compressible and expansible and mounted around the valve tube of the housing;
a column having at least one through hole defined therethrough; and
an upper compression tube being resiliently compressible and expansible, and an interior of the upper compression tube communicating with an interior of the lower compression tube through the at least one through hole of the column;

a bottom valve stem disposed in the lower compression tube and mounted in the valve tube of the housing, a gap formed between the bottom valve stem and the valve tube and not communicating with the interior of the upper compression tube, a bottom end of the bottom valve stem abutting the bottom annular blocking projection of the valve tube to close an open bottom of the valve tube;

a top valve stem disposed in the upper compression tube; and an adapter being hollow and mounted on a top of the outer casing of the housing, the resilient member mounted between the adapter and the actuator, and an interior of the adapter not communicating with the at least one through hole of the column because of the top valve stem;

wherein, a top end of the bottom valve stem is connected to a bottom end of an inner surface of the at least one through hole, a plurality of depressions are formed in the inner surface of the at least one through hole, and each depression has an open bottom communicating with the interior of the lower compression tube and the gap;

the top valve stem extends downward from the interior of the adapter and has
an outer surface; and
a plurality of channels formed in the outer surface of the top valve stem, each channel having an open top communicating with the interior of the adapter, and
a bottom end of the top valve stem abuts the inner surface of the at least one through hole of the column such that the interior of the upper compression tube does not communicate with the at least one through hole of the column.

8. The leak proof needleless medical connector as claimed in claim 7 comprising four components including the housing, the actuator, the resilient member and the adapter, wherein the lower compression tube, the column, the upper compression tube and the bottom valve stem are integrally formed to construct the resilient member.

9. The leak proof needleless medical connector as claimed in claim 3, wherein
the bottom valve stem extends downward from a bottom surface of the column, the column has a plurality of through holes defined therethrough, the through holes are spaced around the bottom valve stem, the bottom valve stem has a flange at its top end, the flange is inserted into a top of the gap such that the gap does not communicate with the through holes of the column;
the bottom annular member of the adapter has
an inner surface; and
a top annular blocking projection extending from the inner surface of the bottom annular member, and
the top valve stem is mounted upward from a top surface of the column, and the enlarged portion abuts the top annular blocking projection of the bottom annular member of the adapter.

10. The leak proof needleless medical connector as claimed in claim 9 comprising five components including the housing, the actuator, the resilient member, the top valve stem and the adapter, wherein the lower compression tube, the column, the upper compression tube and the bottom valve stem are integrally formed to construct the resilient member.

11. The leak proof needleless medical connector as claimed in claim 3, wherein
the lower compression tube has
a lower top plate; and
a lower central hole extending through the lower top plate;
the upper compression tube has
an upper top plate; and
an upper central hole extending through the upper top plate; and
the bottom valve stem extends downward from a bottom surface of the column, the top valve stem extends upward from a top surface of the column, the column has a plurality of through holes defined therethrough, the through holes are spaced around the bottom valve stem and the top valve stem, a top of the valve tube of the housing abuts a bottom surface of the lower top plate of the lower compression tube to urge the lower top plate toward the column to close open bottoms of the through holes of the column such that the through holes do not communicate with the gap, and the enlarged portion abuts an inner surface of the upper central hole of the upper compression tube.

12. The leak proof needleless medical connector as claimed in claim 11 comprising six components including the housing, the actuator, the lower compression tube, the column, the upper compression tube and the adapter, wherein the bottom valve stem and the top valve stem are integrally formed on the column.

13. The leak proof needleless medical connector as claimed in claim 5, wherein walls of the lower and upper compression tubes are waved.

14. The leak proof needleless medical connector as claimed in claim 8, wherein walls of the lower and upper compression tubes are waved.

15. The leak proof needleless medical connector as claimed in claim 10, wherein walls of the lower and upper compression tubes are waved.

16. The leak proof needleless medical connector as claimed in claim 12, wherein walls of the lower and upper compression tubes are waved.

17. The leak proof needleless medical connector as claimed in claim 5, wherein walls of the lower and upper compression tubes are spherical.

18. The leak proof needleless medical connector as claimed in claim 8, wherein walls of the lower and upper compression tubes are spherical.

19. The leak proof needleless medical connector as claimed in claim 10, wherein walls of the lower and upper compression tubes are spherical.

20. The leak proof needleless medical connector as claimed in claim 12, wherein walls of the lower and upper compression tubes are spherical.

* * * * *